July 4, 1972 L. H. SHOESMITH Plant Pat. 3,224

CHRYSANTHEMUM PLANT (HOSTESS)

Filed Oct. 5, 1970

INVENTOR.
LEONARD H. SHOESMITH

Rummler & Snow

Attys.

United States Patent Office

Plant Pat. 3,224
Patented July 4, 1972

3,224

CHRYSANTHEMUM PLANT (HOSTESS)

Leonard H. Shoesmith, Westfield, Woking Surrey, England, assignor to Pan-American Plant Company, Chicago, Ill.

Filed Oct. 5, 1970, Ser. No. 78,309
Int. Cl. A01h *5/00*
U.S. Cl. Plt.—76 1 Claim

ABSTRACT OF THE DISCLOSURE

A new variety of greenhouse pot-plant type of chrysanthemum distinguished by the pink-purple color of its profusely produced blooms, its compact habit of growth which breaks freely with many branches, and its uniform, dependable response to protoperiod control for flowering at any preselected time of the year.

BACKGROUND OF THE NEW PLANT

My new chrysanthemum plant originated as a seedling product of random crosses of various greenhouse varieties of the pot-plant type made during extensive breeding efforts carried on by me at West Chicago, Ill., with the object of developing improved varieties of chrysanthemums for greenhouse pot-plant culture.

This seedling was selected by me for propagation and test because of its profuse production of distinctively colored blooms on a compact, much branched plant and subsequent asexual propagation of the plant by me at West Chicago, Ill., by means of vegetative cuttings, has showed that this plant also has excellent response to photoperiod control, a dependable nine week response period, and ability to be flowered at any selected time the year around.

Asexual propagation of this new plant at West Chicago, Ill., and at Cortez, Fla., through many generations, has showed conclusively that all of the before mentioned advantages and characteristics come true from generation to generation and are firmly fixed.

DESCRIPTION OF THE DRAWINGS

My new variety of chrysanthemum plant is illustrated by the accompanying drawing in which the principal figure shows the entire plant in full bloom and in full color, as nearly true as it is reasonably possible to obtain by conventional photographic reproduction, the ink drawn figures show the configuration of typical specimens of leaves of the new plant, and the color patch is a hand-painted strip having the true mallow purple color of the flowers shown.

DESCRIPTION OF THE NEW PLANT

Figure 1:
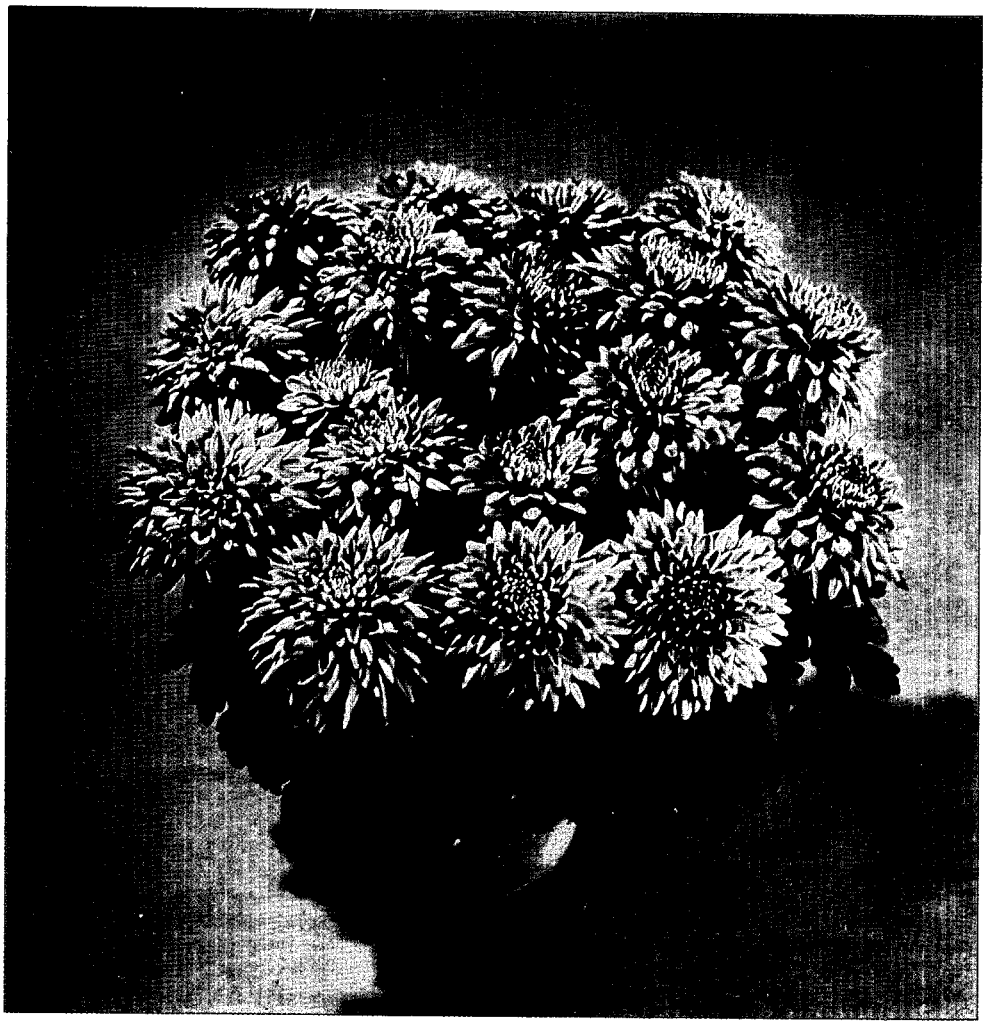
Figure 2:
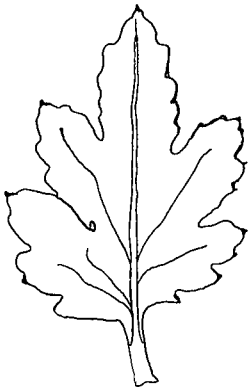
Figure 3:
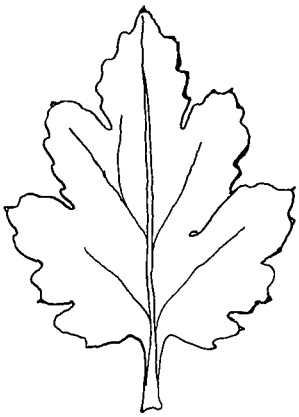

The following is a detailed description of my new variety of chrysanthemum plant with color designations according to the Horticultural Colour Chart issued by the British Colour Council.

*The plant*

Origin: Seedling—selected from random crosses.
Parentage: Unknown.
Classification: Botanic—*Chrysanthemum morifolium*—commercial—Greenhouse pot-plant.
Form: Pot-plant bush.
Height: 12 inches.
Growth: Terminal. Vigorous with good strength and sturdiness, upright and much branching.
Foliage: Quantity: abundant with about 6 leaves per 6 inch stem.

*Leaf size.*—Approximately 4 to 4½ inches long by 3 to 3¾ inches wide.
*Shape.*—Lanceolate, lobed and slightly serrated.
*Texture.*—Soft—rubbery with satiny aspect.
*Color.*—Upper side—Spinach Green 0960—under side—Spinach Green 0960/3.
*Ribs and veins.*—Almost palmately veined.
*Rachis.*—Pronounced.
*Petioles.*—About 1 inch long.

*The bud*

Form: Globular with flat bottom and oval top—diameter—½ inch.
Opening: Bud opens slowly.
Color: When sepals first divide—Pastel Mauve 433—when petals begin to unfurl—Mauve 633/1.
Sepals: Stand up—Color:
*Inside.*—Scheeles Green 860.
*Outside.*—Scheeles Green 860.
Calyx: Shape—globular. Calyx does not split. Aspect—smooth.
Peduncle: About 2 inches long, erect and slightly tomentose—Color—Scheeles Green 860.

*The flower*

Blooming characteristic: Can be flowered year around with photoperiod control.
Response: Dependable nine week response.
Natural season: Flowering in late October.
Size: About 2½ to 3 inches in diameter (disbudded).
Borne: Singly upon disbudding.
Shape: Cup shaped when bloom first opens.
Petalage: Petals are many in number and disposed in composite arrangement.
*Form.*—Ray floret about 2 inches long.
*Color.*—Outer petal—Mallow Purple 630/2 with Primrose Yellow 601/3 at the base—inside petal—Mallow Purple 630/2—reverse side—Amarath Rose 530/2.
*Texture.*—Soft appearance—Satiny.
Peduncle: Sturdy and upright, and about 2 inches long—color: Scheeles Green 860.
Discoloration: Fades to a lighter color as the full bloom ages.
Persistence: The flower and its petals hang on and dry.
Lasting Quality: Long lasting on the plant. Not used as a cut flower.

*Reproductive organs*

Stamens: Plant does not seem to possess anthers or filaments. Pollen—none found.
Pistils: One for each ray floret about 5/16 inch long.
Stigmas: Color—Straw Yellow 604.

The principal distinctions of this new variety of greenhouse pot-plant chrysanthemum appear to reside in its short compact much-branching growth habit and in its uniform, dependable nine-week response producing a well-developed free-blooming plant. This plant breaks freely and blooms profusely with medium sized blossoms borne one to a stem when disbudded.

I claim:

1. A new and distinct variety of chrysanthemum plant of the greenhouse pot-plant type, substantially as herein shown and described, characterized by the generally pinkish-purple color of its many blossoms, its vigorous upright and compact growth habit, its capability of being flowered at any time of the year, and its dependable nine week response to photoperiod control.

No references cited.

ROBERT E. BAGWILL, Primary Examiner